United States Patent [19]
Josiah et al.

[11] Patent Number: 6,146,842
[45] Date of Patent: Nov. 14, 2000

[54] HIGH-THROUGHPUT SCREENING ASSAYS UTILIZING METAL-CHELATE CAPTURE

[75] Inventors: Serene Josiah, Cambridge; Michael Boisclair, Brookline, both of Mass.

[73] Assignee: Mitotix, Inc., Cambridge, Mass.

[21] Appl. No.: 09/398,341

[22] Filed: Sep. 17, 1999

Related U.S. Application Data

[60] Provisional application No. 60/101,196, Sep. 21, 1998.

[51] Int. Cl.$^7$ ............................. C12Q 1/00; C12Q 1/48; A61K 38/04
[52] U.S. Cl. .............................. 435/15; 435/4; 530/329; 530/300; 530/200
[58] Field of Search ........................ 435/15, 4; 530/329, 530/300, 200

[56] References Cited

FOREIGN PATENT DOCUMENTS 9726246  7/1997  WIPO .

OTHER PUBLICATIONS

Burger and Still: "Synthetic Ionophores. Encoded Combinatorial Libraries of Cyclen–based Receptors for Cu $^{2+}$ and Cu $^{2+}$", J. Org. Chem. 60:7382–7383 (1995).
Casey, J. Patrick: "Biochemistry of Protein Prenylation", Journal of Lipid Research 33: 1731–1740 (1992).
Casey et al., "Enzymatic Modification of Proteins With a Geranylgeranyl Isoprenoid", Proc. Natl. Acad. Sci. USA, 88:8631–8635, (Oct. 1991).
Clarck Steven: "Protein Isoprenylation and Methylation at Carboxyl–Terminal Cysteine Residues", Ann. Rev. Biochem. 61:355–386 (1992).
Farnsworth et al., "Identification of Geralnylgeralnyl–Modified Proteins in Hela Cells", Science 247:320–322(Jan. 19, 1990).
Francis et al., "Combinatorial Approach to the Discovery of Novel Coordination Complexes", J. Am. Chem. Soc. 118:8983–8984 (1996).
Glomset et al., "Prenyl Proteins in Eukaryotic Cells: A New Type of Membrane Anchor", Trends in Biochemical Sciences, 15:139–142 (1990).
Goodman et al., "A Combinatorial Library Approach to Artificial Receptor Design", J. Am. Chem. soc. 117:11610–11611, (1995).
Horwitz et al., "Ligand Design approach for Securing Robust Oxidation Catalysts", J. Am.Chem. Soc. 120:4867–4868, (1998).
Maltese A. William: "Prosttranslational Modification of Proteins by Isoprenoids in Mammalian Cells", The Faseb Journal, 4:3319–3328(Dec. 1990).
Menard et al., "Rac1, A Low–molecular–mass GTP–binding–Protein with High Intrinsic GTPase Activity and Distinct Biochemical Properties", European Journal of Biochemistry, 206:537–546 (1992).
Moomaw and Casey ;"Mammalian Protein Geranylgeranyltransferase: Subunit Composition and Metal Requirements", The Journal of Biological Chemistry 267(24): 17438–17443 (Aug. 25, 1992.
Moores et al., "Sequence Dependence of Protein Isoprenylation", The Journal of Biological Chemistry 266(22):14603–14610 (Aug. 5, 1991).
Reiss et al., : Divalent Cation and Prenyl Pyrophosphate Specificities of the Protein Farnesyltransferase from Rat Brain, a Zinc Metalloenzyme, The Journal of Biological Chemistry 267 (9):6403–6408 (1992).
Torrado et al., "Exploiting Polypeptide Motifs for the Design of selective Cu(II) Ion Chemosensors", J. Am. Chem. Soc. 120: 609–610 (1998).
Yokoyama et al., "A Protein Geranylgeranyltransferase from Bovine Brain: Implications for Protein Prenylation specificity", Proc. Natl. Acad. Sci. USA 88: 5302–5306 (Jun. 1991).

*Primary Examiner*—Louise N. Leary
*Attorney, Agent, or Firm*—Foley, Hoag & Eliot, LLP; Matthew P. Vincent, Esq.; David P. Halstead

[57] ABSTRACT

A high throughput enzyme screen has been developed which relies on metal chelate interaction for capture of the product of the enzymatic reaction. In the present assay system, a detectable moiety is attached to a substrate having a chelating capturable moiety, which can be captured by an immobilized metal. Detection is effected due to the presence of a detectable label on the reaction product immobilized on the solid phase. Only signal associated with tagged protein bound to the solid phase is detected. The present assay can reliably measure enzyme activity, and has high reproducibility, which benefits high throughput screening.

19 Claims, 4 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
    (A) LENGTH: 6 amino acids
    (B) TYPE: amino acid
    (D) TOPOLOGY: linear   (ii) MOLECULE TYPE: protein   (xi) SEQUENCE DESCRIPTION: SEQ ID NO:1:

```
His His His His His His
  1               5
```

HIGH-THROUGHPUT SCREENING ASSAYS UTILIZING METAL-CHELATE CAPTURE

RELATED APPLICATIONS

This application is based on U.S. Provisional Application No. 60/101,196, filed Sep. 21, 1998, hereby incorporated by reference.

FIELD OF THE INVENTION

The invention relates to a high-throughput enzyme screening assay which utilizes capture of a metal-chelate by a metal-bearing substrate for detection of the product. More particularly, the invention relates to high-throughput screens in which a radioactively labeled donor group which has been enzymatically transferred to a substrate tagged with a metal-chelating group can be detected on a metal-derivatized resin or other substrate.

BACKGROUND OF THE INVENTION

Covalent modification by isoprenoid lipids (prenylation) contributes to membrane interactions and biological activities of a rapidly expanding group of proteins (Maltese, *FASEB J.* 4:3319 (1990); Glomset et al, *Trends Biochem. Sci.*, 15:139 (1990)). Either farnesyl (15-carbon) or geranylgeranyl (20-carbon) isoprenoids can be attached to specific proteins, with geranylgeranyl being the predominant isoprenoid found on proteins (Farnsworth et al, *Science*, 247:320 (1990)). The prenyltransferase, protein geranylgeranyltransferase type-I (GGTase-I), transfers a geranylgeranyl group from the prenyl donor geranylgeranyl diphosphate to the cysteine residue of substrate proteins containing a C-terminal CAAX-motif in which "A" is any amino acid, including an aliphatic amino acid, and the "X" residue is leucine (Clarke, *Ann. Rev. Biochem.*, 61:355 (1992); Casey, *J. Lipid. Res.*, 330:1731 (1992)). Known targets of GGTase-I include gamma-subunits of brain heterotrimeric G proteins and Ras-related small GTP-binding proteins such as Rac1, Rac2, Rap1A and Rap1B (Menard et al, *Eur. J. Biochem.*, 206:537 (1992); Casey et al, *Proc. Natl. Acad. Sci, USA*, 88:8631 (1991); Moores et al, *J. Biol. Chem.*, 136:14603 (1991)).

Additionally, short peptides encompassing the CAAX motif of these substrates can also be recognized by the enzyme (Casey et al, *Proc. Natl. Acad. Sci. USA*, 88:8631 (1991); (Moores et al, *J. Biol. Chem.*, 136:14603 (1991); Yokoyama et al, *Proc. NatL. Acad. Sci. USA*, 88:5302 (1991)). Immobilization of one such peptide for use as an affinity matrix has led to the isolation of GGTase-I from bovine brain (Moomaw and Casey, *J. Biol. Chem.*, 267:17438 (1992)). The purified enzyme contains two subunits with molecular masses of 48 kDa and 43 kDa, which have been designated, respectively, as alpha and beta (henceforth designated beta [GGI]). GGTase-I is dependent on both $Mg^{2+}$ and $Zn^{2+}$ for optimal activity. Demonstration of the $Zn^{2+}$ dependence required prolonged incubation against, or purification in the presence of, a chelating agent. This property has led to the designation of GGTase-I as a zinc metalloenzyme (Moomaw and Casey, *J. Biol. Chem.* Id.).

The properties of GGTase-I are similar to those of a related enzyme, protein farnesyltransferase (FTase). FTase transfers the prenyl moiety from farnesyl diphosphate to the cysteine residue of substrate proteins. FTase protein substrates, like those for GGTase-I, possess a C-terminal CAAX motif. The "X" residue of mammalian FTase substrates, however, is generally methionine, serine or glutamine as opposed to leucine for GGTase-I substrates (Moores et al, *J. Biol. Chem.*, 136:14603 (1991); Moomaw and Casey, *J. Biol. Chem.*, 267:17438 (1992)). Substrates for FTase include p21 (ras) protein, lamin B and several proteins involved in visual signal transduction (Clarke, *Ann. Rev. Biochem.*, 61:355 (1992)). Like GGTase-I, FTase is dependent upon $Mg^{2+}$ and $Zn^{2+}$ ions for optimal activity (Reiss et al, *J. Biol. Chem.*, 267:6403 (1992)).

Purified mammalian FTase is composed of two nonidentical subunits, alpha and beta (henceforth designed beta F), with apparent molecular masses of approximately 48 kDa and 46 kDa, respectively, on SDS-PAGE (Reiss et al, *Cell* 62:81 (1990)). cDNA clones encoding the FTase alpha and beta F subunits have been isolated and their deduced amino acid sequences are homologous to the Saccharomyces cerevisiae proteins Ram2 and Dpr1/Ram1, respectively, which encode the subunits of yeast FTase (Moores et al, *J. Biol. Chem.*, 136:14603 (1991); Chen et al, *Proc. Natl. Acad Sci. USA*, 88:11368 (1991); Kohl et al, *J. Biol. Chem.*, 266:18884 (1991); He et al, *Proc. Natl. Acad. Sci. USA*, 88:11373 (1991)).

The Ras family of proteins are important in the signal transduction pathway modulating cell growth. The protein is produced in the ribosome, released into the cytosol, and post-translationally modified. The first step in the series of post-translational modifications is the alkylation of $Cys^{168}$ with farnesyl or geranylgeranyl pyrophosphate in a reaction catalyzed by prenyl transferase enzymes such as farnesyl transferase and geranylgeranyl transferase (Hancock, J. F., et al., *Cell*, 57:1167–1177 (1989)). Subsequently, the three C-terminal amino acids are cleaved (Gutierrez, L., et al., *EMBO J.* 8:1093–1098 (1989)), and the terminal Cys is converted to a methyl ester (Clark, S., et al., *Proc. Nat'l Acad Sci.* (*USA*), 85:4643–4647 (1988)). Some forms of Ras are also reversibly palmitoylated on cysteine residues immediately N-terminal to $Cys^{168}$ (Buss, J. E., et al., *Mol. Cell. Biol.*, 6:116–122 (1986)). It is believed that these modifications increase the hydrophobicity of the C-terminal region of Ras, causing it to localize at the surface of the cell membrane. Localization of Ras to the cell membrane is necessary for signal transduction (Willumsen, B. M., et al., *Science*, 310:583–586 (1984)).

Oncogenic forms of Ras are observed in a relatively large number of cancers including over 50 percent of colon cancers and over 90 percent of pancreatic cancers (Bos, J. L., *Cancer Research*, 49:4682–4689 (1989)). These observations suggest that intervention in the function of Ras mediated signal transduction may be useful in the treatment of cancer.

Previously, it has been shown that the C-terminal tetrapeptide of Ras is a "CAAX" motif (wherein C is cysteine, A is an aliphatic amino acid, and X is any amino acid). Tetrapeptides having this structure have been shown to be inhibitors of prenyl transferases (Reiss, et al., *Cell*, 62:81–88 (1990)). Poor potency of these early farnesyl transferase inhibitors has prompted the search for new inhibitors with more favorable pharmacokinetic behavior (James, G. L., et al., *Science*, 260:1937–1942 (1993); Kohl, N. E., et al., *Proc. Nat'l Acad. Sci. USA*, 91:9141–9145 (1994); deSolms, S. J., et al., *J. Med. Chem.*, 38:3967–3971 (1995); Nagasu, T., et al., *Cancer Research*, 55:5310–5314 (1995); Lerner, E. C., et al., *J. Biol. Chem.*, 270:26802–26806 (1995); Lerner, E. C., et al., *J. Biol. Chem.*, 270:26770 (1995); and James, et al., *Proc. Natl. Acad. Sci. USA*, 93:4454 (1996)).

Recently, it has been shown that a prenyl transferase inhibitor can block growth of Ras-dependent tumors in nude mice (Kohl, N. E., et al., *Proc. Nat'Acad. Sci. USA*, 91:914–9145 (1994)). In addition, it has been shown that over 70 percent of a large sampling of tumor cell lines are inhibited by prenyl transferase inhibitors with selectivity over non-transformed epithelial cells (Sepp-Lorenzino, I., et al., Cancer Research, 55:5302–5309 (1995)).

A traditional approach to studying enzymatic activity based on protein-protein interactions is via a standard TCA precipitation assay methodology. Bollag, et al., (1996), *Protein Methods* (2$^{nd}$ Ed.) Wiley-Liss, Inc., New York, N.Y. In principle, the modification of a substrate can be detected through radioactive tagging of the substrate and its capture onto glass fiber filters. Total protein is captured by TCA precipitation. In a heterogeneous assay system, limitations include the necessity for washing steps, use of corrosive reagents, such as trichloroacetic acid (TCA) and additional steps such as use of adapter plates and the addition of liquid scintillant. This assay format allows for accurate measurements of modified proteins, but is severely limiting for automated high-throughput screening (HTS).

SUMMARY OF THE INVENTION

The present invention comprises an assay using metal-chelate capture technology to rapidly detect substrates which are modified by an enzyme. The use of the metal-chelate capture methodology allows the detection of signal from radioactively modified tagged proteins which bind to the surface of a metal-bearing solid support. Washing steps to remove unbound radioactivity from a given reaction well are usually unnecessary. The present assay utilizing metal-chelate capture detection technology provides robust assays which can be readily adapted to automation for a drug discovery program. The present assay methodologies allow development of homogenous assay systems for detecting enzymatic activity which eliminate the need for washing steps, adapter plates and the addition of liquid scintillant, and which can be used in an HTS mode.

The present method comprises the following general steps: (a) combining a test compound with an enzyme capable of catalyzing the transfer of a detectable moiety to a substrate, a donor labeled with the detectable label, and a substrate specific for the enzyme comprising a metal-chelating moiety, and incubating the mixture under conditions sufficient to promote the enzymatic reaction; (b) stopping the reaction after an appropriate amount of time and contacting the reaction mixture with a metal-derivatized solid phase under conditions sufficient to promote reaction of the immobilized metal and the chelating moiety; and (d) detecting the signal generated.

In one embodiment, the invention comprises an assay for compounds which inhibit the activity of a prenyl transferase enzyme. The present method comprises the following steps: (a) combining a test compound with a prenyl transferase, a radioactively-labeled donor group and a substrate tagged with a metal-chelating moiety, and incubating the mixture under conditions sufficient to promote reaction of the components; (b) stopping the reaction after an appropriate amount of time and contacting the reaction mixture with a metal-derivatized substrate having an immobilized scintillant; and (d) detecting the radioactivity signal generated.

The assay may be used to screen for test compounds which affect the activity of an enzyme, e.g., compounds which potentiate or inhibit the enzyme's activity. The change in the enzyme's activity relative to a control is indicative of the effect of the compound. For example, in the currently preferred embodiment of the present assay, the a prenyl transferase system is used to screen for compounds which inhibit the prenyl transferase's activity. In this embodiment, the enzyme comprises a prenyl transferase enzyme, e.g., farnesyl or geranylgeranyl transferase. The donor group may be any prenyl group capable of being transferred to a substrate via the activity of the enzyme, e.g., farnesyl or geranylgeranyl diphosphate. The donor group is labeled with a detectable label. The substrate can be any protein or peptide which is a substrate for a prenyl transferase enzyme. Such substances include, for example, proteins or peptides containing a C-terminal CAAX-motif in which "A" is any amino acid, including an aliphatic amino acid, and the "X" residue is leucine, methionine, serine, alanine or glutamine. The substrate is tagged with a chelating moiety thereby permitting the substrate to be captured by the metal-derivatized solid phase. In the currently preferred embodiment, the metal chelating moiety comprises a short amino acid sequence which is capable of reacting with or complexing with a metal present on the solid phase. An amino acid sequence comprising six consecutive histidine residues which is capturable by nickel currently is preferred for this purpose.

Kits for performing the assay of the present invention also form a part of this invention. The kits comprise an enzyme capable of catalyzing the transfer of a detectable moiety to a substrate, a donor substance labeled with the detectable label, and a substrate specific for the enzyme comprising a metal-chelating moiety. The kits also optionally may include a metal-derivatized solid phase. Alternatively, a commercially available metal-derivatized solid phase, such as those described herein, may be used.

It will be readily apparent that the assay system of the present invention also can be readily adapted for use with enzyme systems other than prenyl transferase.

DETAILED DESCRIPTION OF THE INVENTION

The present assay system utilizes a metal chelating detection system to detect the product of an enzyme-catalyzed reaction. In the present assay system, the enzyme substrate comprises a capturable metal-chelating moiety. The enzyme catalyzes a reaction which causes a radioactive label to be attached to the substrate. The labeled substrate then is captured by chelation of the chelating moiety to an immobilized metal. The immobilized labeled product then can be detected.

The present method comprises the following steps: (a) combining a test compound with an enzyme capable of catalyzing the transfer of a detectable moiety to a substrate, a donor substance labeled with the detectable label, and a substrate specific for the enzyme comprising a metal-chelating moiety, and incubating the mixture under conditions sufficient to promote the enzymatic reaction; (b) stopping the reaction after an appropriate amount of time and contacting the reaction mixture with a metal-derivatized solid phase; and (d) detecting the signal generated.

The assay may be used to screen for test compounds which affect the activity of an enzyme, e.g., compounds which potentiate or inhibit the enzyme's activity. The change in the enzyme's activity relative to a control is indicative of the effect of the compound.

In the currently preferred embodiment of the present assay, a prenyl transferase system is used to screen for compounds which inhibit the prenyl transferase's activity. In this embodiment, the enzyme comprises a prenyl transferase enzyme, e.g., farnesyl or geranylgeranyl transferase. The donor group may be any prenyl group capable of being transferred to a substrate via the activity of the enzyme, e.g., farnesyl diphosphate or geranylgeranyl diphosphate. The donor group is labeled with a detectable label. The label can be any detectable label, e.g., a radioactive label, a chemiluminescent label, a fluorescent label, etc. In the preferred embodiment, the donor group is labeled with a radioactive isotope.

The substrate can be any protein or peptide which is a substrate for a prenyl transferase enzyme. Such substances include, for example, proteins or peptides containing a C-terminal CAAX-motif in which "A" is any amino acid, including an aliphatic amino acid, and the "X" residue is leucine, methionine, serine, alanine or glutamine. Examples of substrates which can be used in prenyl transferase systems include known targets of GGTase-I include gamma-subunits of brain heterotrimeric G proteins and Ras-related small GTP-binding proteins such as Rac1, Rac2, Rap1A and Rap1B. Short peptides encompassing the CAAX motif of these substrates can also be recognized by the enzyme. Substrates for FTase include p21(ras) protein, lamin B and several proteins involved in visual signal transduction. The substrate is tagged with a chelating moiety thereby permitting the substrate to be captured by the metal-derivatized solid phase. In the currently preferred embodiment, the metal chelating moiety comprises a short amino acid sequence which is capable of reacting with or complexing with a metal present on the solid phase. An amino acid sequence comprising six consecutive histidine residues (6xHis) which is capturable by nickel is currently preferred for this purpose.

In the currently preferred embodiment of the present invention, the detectable label is a radioactive material which reacts with a scintillating agent present on the solid phase. In this embodiment, the solid phase comprises a solid support having an immobilized metal and comprising a scintillant disposed or coated on the surface of the solid phase. A suitable solid phase is available in the form of a FlashPlate™ (NEN Life Sciences Products Catalog Numbers SMP300). The FlashPlate™ microplate is a 96-well white polystyrene plate with polystyrene-based scintillant-coated wells designed for high-volume, in-plate assays where the signal comes from radioactive molecules. A number of isotopes can be used in conjunction with FlashPlates™, including $^3$H, $^{14}$C, $^{35}$S, $^{125}$I, $^{45}$Ca, $^{33}$P and $^{32}$P. FlashPlate™ microplates are designed for use with the Packard TopCount® Microplate Scintillation and Luminescence Counter, though other scintillation counters can be readily adapted for reading such plates. In addition, the immobilized metal may be in a form other than a plate, for example, a column or flow-through bed design also may be used. Solid phase material such as beads, sheets, fibers or other configuration may be used in lieu of a microtitre plate.

In addition to the 6xHis tag described in the appended examples, the practitioner of the instant method will recognize that there exists a wide range of possible metal/ion chelating peptide sequences which can be used to generate the capturable fusion proteins. In general, the chelating peptide should have minimal effect on the structure of the attached protein structure. An advantage to using the 6xHis tag is that is much smaller than most other affinity tags (e.g., relative to glutathione S-transferase, Protein A and maltose binding protein). Moreover, the 6xHis tag is uncharged at physiological pH, so that it is less likely to interfere with other aspects of the subject assay. The generation of equivalent chelating peptides for use in the subject method can be carried out using such protocols as described in, for example, Torrado et al., (1998) "Exploiting Polypeptide Motifs for the Design of Selective Cu(II) Ion Chemosensors", *J. Am. Chem. Soc.*, Vol. 120:609–610; Burger et al., (1995) "Synthetic Ionophores. Encoded Combinatorial Libraries of Cyclen-based Receptors for Cu2+ and Co2+", *J. Org. Chem.*, 60:7382–7382, 1995; Francis, M., et al., (1996) "Combinatorial Approach to the Discovery of Novel Coordination Complexes", *J. Am. Chem. Soc.*, 118:8983–8984; Goodman et al., (1995) "A Combinatorial Library Approach to Artificial Receptor Design", *J. Am. Chem. Soc.*, 117:11610–11611; Horwitz et al., (1998) "Ligand Design Approach for Securing Robust Oxidation Catalysts", *J. Am. Chem. Soc.*, 120:4867–4868; Jones (1994) "Applications Of Encoded Synthetic Libraries In Ligand Discovery", *Polym. Prep.*, 35:981–2; Lam et al., (1992) "A New Type of Synthetic Peptide Library for Identifying Ligand-Binding Activity—Generation and Use of Synthetic Peptide Combinatorial Libraries for Basic Research and Drug Discovery", *Organic Chemistry*, 5:71–72.

Suitable metals for chelation of peptide sequences include platinum, palladium, iron, nickel, ruthenium and rhodium. In other preferred embodiments, calcium ($Ca^{+2}$) is used as the metal in lieu of nickel.

The invention is further illustrated by the following Examples, which are not intended to be limiting in any way.

EXAMPLES

Figure 1:
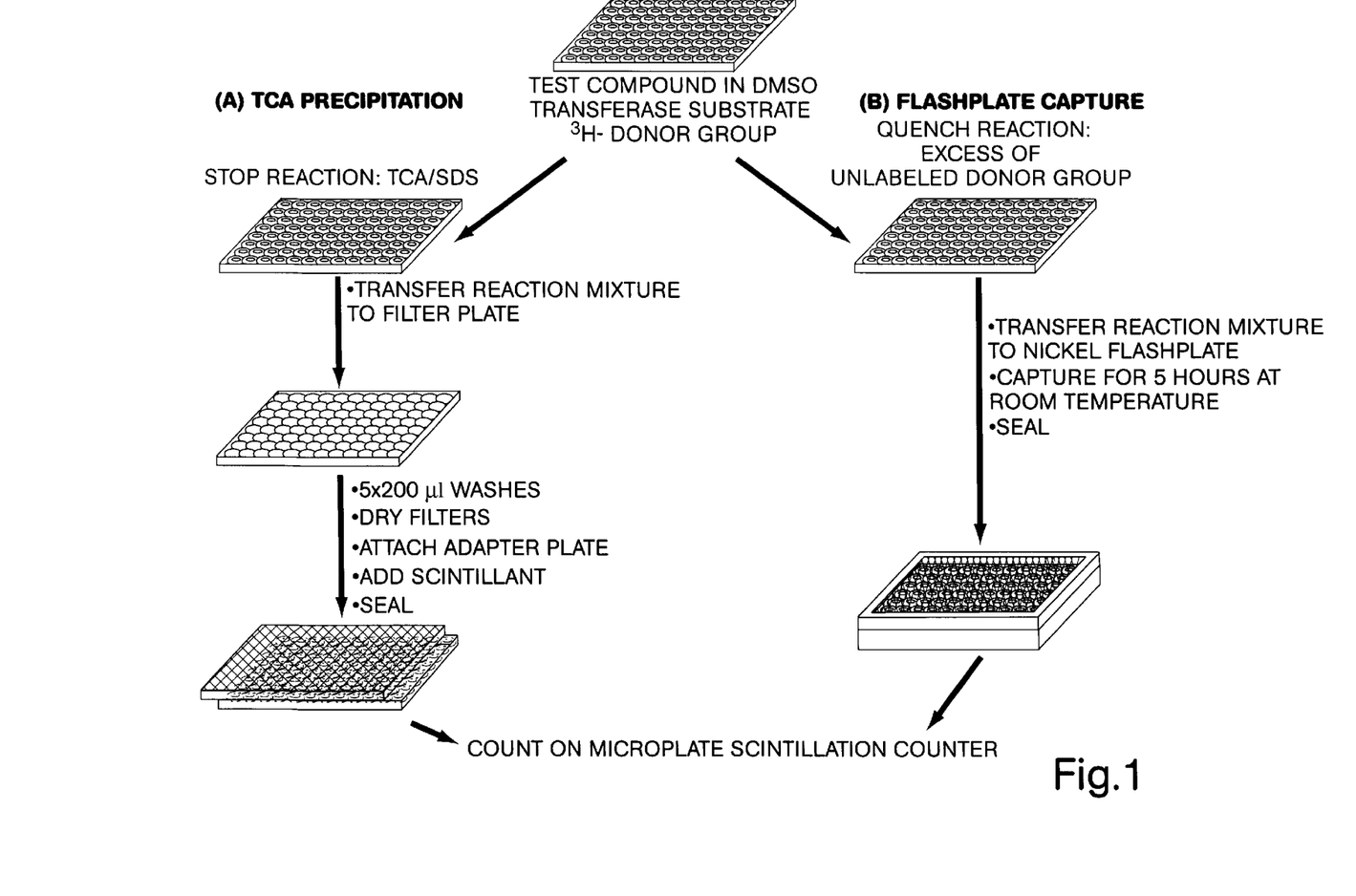
FIG. 1 is a schematic of an assay for transferase activity using TCA precipitation and FlashPlate methodologies.

TCA precipitation and the present chelate capture methodologies were compared by measuring prenyl transferase enzymatic activity using a nickel FlashPlate™. In order to allow for solution phase reactions, a two plate procedure was used for both methodologies. Enzyme reactions were performed in a 96-well plate (assay plate). Once the reaction was completed, the reaction mixture was transferred onto a second 96-well plate (capture plate): glass fiber filter plate for TCA precipitation method and nickel FlashPlate™ for the FlashPlate™ method. The principle of the TCA and FlashPlate™ methodologies is illustrated in FIG. 1. As shown in FIG. 1, reactions were performed in standard v-bottom 96-well plates. The reactions were stopped with the addition of TCA/SDS (in the TCA precipitation method) or quenched with the addition of excess unlabeled donor group (in the FlashPlate™ method). Stopped or quenched reaction mixtures were transferred to a filter plate or FlashPlate™ and the plates processed as shown.

Methods
TCA Precipitation Method:

In the following method, enzyme reactions were performed in a 96-well polypropylene plate (Nunc, cat. no. 442587). Geranylgeranyl transferase enzyme, $^3$H-donor group (geranylgeranyl diphosphate) and a substrate peptide tagged with a 6-histidine tail were incubated together for 30 minutes at room temperature. The substrate was a peptide sequence synthesized with a 6-histidine terminal sequence (Anaspec, San Jose, Calif.). This peptide was pre-phosphorylated by cAMP dependent protein kinase (PKA). The reactions were stopped with the addition of a 1:1 mixture of 10% SDS and 75% TCA. The stopped reactions were incubated at room temperature for 15 minutes, transferred to a 96-well filter plate (Millipore, cat. no. MAFB NOB) and washed five times with 200 µl additions of 10% TCA. The filter plate plastic back was discarded and the filters were air-dried. Filter plates were fitted into adapter plates (Packard, cat. no. 6005178). Scintillation fluid was added to each well (Packard, cat. no. 6613621). The plates were sealed and read in a microplate scintillation counter (TOPCOUNT, Packard).

FlashPlate™ Method:

Enzyme reactions were performed as described above in a 96-well polypropylene plate. The reactions were quenched with the addition of a solution containing, excess molar concentration of unlabeled donor group and 2% BSA. The quenched reaction was transferred to a nickel chelate Flash-Plate™ Plus: SMP107 (New England Nuclear, Billerica, Mass.). Plates were incubated 5 hours to overnight at room temperature. When testing compounds, plates were rinsed once with 200 µl of 50 mM Tris, HCl (pH 7.5). Plates were sealed and read in a microplate scintillation counter (TOPCOUNT, Packard).

Reagent Handling:

Unless stated, reagents were delivered to a 96-well plate utilizing a Quadra 120-96 pipetting station (Tomtec). This station was fitted with a Millipore filter plate washer to allow both TCA precipitation and FlashPlate™ methods to be run.

Optimization of Capture of Histidine Tagged Proteins on Nickel FlashPlate™:

The effects of various blocking reagents and common laboratory detergents on the interaction of histidine tagged protein to a nickel FlashPlate™ were evaluated in order to determine favorable binding conditions.

Use of Blocking Reagents:

Plates were blocked with PBS (Dulbecco's PBS 17-515Q) containing the following additions: 0.1% BSA (Pentex 82-045-2), 1% BSA, 1% BSA and 10% β-Lactose (Sigma, L3750), 5% casein (Sigma, C8654), and 3% fish gel (Norland Scientific) diluted with distilled H$_2$O. The plates were blocked with 300 µl per well overnight at room temperature and washed once with PBS. For the blocked plates, 3H-donor was diluted to 0.1 µM in either PBS or PBS with 0.01% Tween-20 (Sigma, P-1379). For an unblocked plate, $^3$H-donor was diluted to 0.1 µM in the following buffers: PBS, PBS with 0.1% BSA, PBS with 1% BSA, PBS with 1% BSA and 10% β-Lactose, PBS with 5% casein and 3% fish gel in distilled H$_2$O. For another unblocked plate, the $^3$H-donor was diluted in the above buffers with the addition of 0.01% Tween. For all plates, 100 µl of $^3$H-donor solution was added to each well. The plates were incubated at room temperature for 4 hours or overnight and read in a microplate scintillation counter (TOPCOUNT, Packard).

Effect of Detergents and DMSO:

The kemptide peptide sequence (LRRASLG) was synthesized with a 6-histidine terminal sequence (Anaspec, San Jose, Calif.). This peptide was pre-phosphorylated by cAMP dependent protein kinase (PKA). The phosphorylated peptide was diluted in PBS as well as a series of concentrations of the following reagents diluted in PBS: Tween 20, Triton X-100, NP-40 and dimethylsulfoxide (DMSO). The peptide was then added to the nickel FlashPlate™ and incubated overnight at room temperature.

Effect of DTT:

Polyhistidine was iodinated (NEN, Billerica, Mass.) and diluted in PBS containing 0.1% BSA and a range of concentrations of dithiothreitol (DTT). The [$^{125}$I]polyhistidine solution was added to the nickel FlashPlate™ and incubated overnight at room temperature.

Results

Figure 2A:
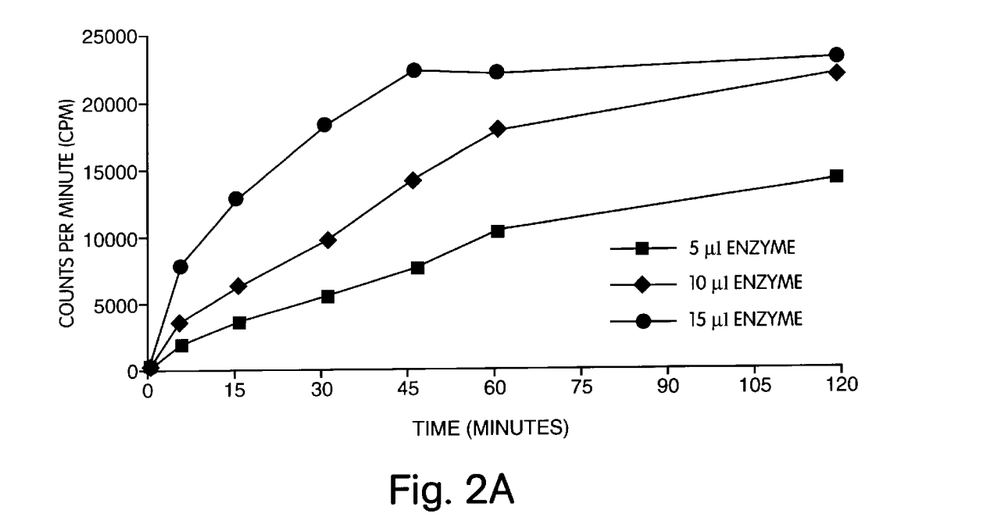
FIG. 2A is a graph showing the time course of transferase activity using the TCA precipitation method.
Figure 2B:
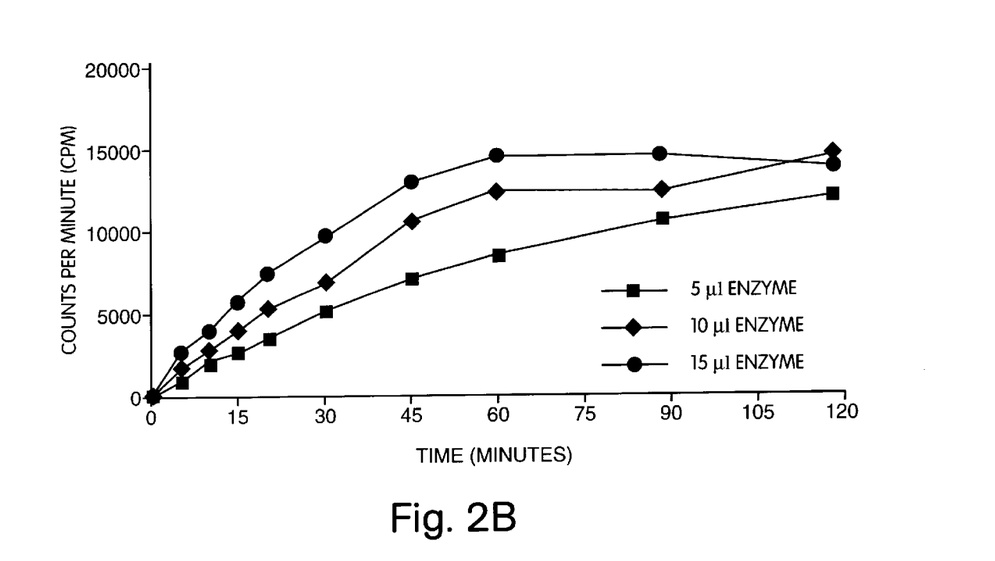
FIG. 2B is a graph showing the time course of transferase activity using the FlashPlate method.

Prior to evaluating TCA precipitation and FlashPlate™ methodologies for HTS, it was necessary to establish that the transferase assay was measuring enzymatic activity. Prenyl transferase activity was titrated and measured by TCA precipitation or FlashPlate™ methodologies. The time course of enzymatic activity was measured by inhibiting the reaction at specific time points by the addition of SDS for TCA precipitation methodology (FIG. 2A) or excess unlabeled donor group for FlashPlate™ methodology (FIG. 2B). The reaction rate was dependent upon enzyme concentration, indicating that the assay is measuring enzyme catalyzed conversion of substrate to product. The time course of transferase activity was also dependent upon enzyme concentration. A linear reaction time course of 45 to 60 minutes was observed for a given concentration of enzyme. The time course of reaction as measured by both TCA precipitation and FlashPlate™ methodologies, was comparable.

Transferase activity can be measured by either TCA precipitation or FlashPlate™ methodologies, however, both are not suitable for HTS. Acceptable criteria for HTS are (i) high reproducibility of the assay ($\leq$10% intra-plate CV) (ii) robust signal to noise (S:N) ratio ($\geq$20:1) and (iii) reproducible detection of inhibition by standard inhibitors.

FlashPlate methodology requires capture of reaction product to coated wells. Therefore, it is important to establish that the assay conditions do not interfere with the capture process. In addition, the assay should be tolerant of DMSO, an universal solvent, in order to facilitate compound testing. Several organic solvents and common assay laboratory reagents were tested on nickel FlashPlates for their effect in preventing capture of a histidine-tagged peptide. The binding interaction of a histidine tagged peptide to the nickel FlashPlate™ was evaluated in the presence of these reagents. The maximal concentration of a given reagent which did not interfere with binding of the histidine tagged peptide to the FlashPlate™ is indicated. The results are shown in Table 1.

TABLE 1

Tolerance of nickel FlashPlates ™ to common assay reagents

| Reagent | Maximum concentration tolerated in assay |
|---|---|
| Tween-20 | 1% |
| Triton-X-100 | 1% |
| NP 40 | 1% |
| EtOH | <25% |
| MeOH | <25% |
| DMSO | 10% |
| DTT | 1 mM |

In addition to the above, the use of BSA, casein and fish gel as blocking reagents was shown to be suitable at 2%, 5% and 3%, respectively (data not shown). The following conditions did not interfere with histidine-nickel interaction and were suitable for assay of transferase activity: a final assay concentration of 10% DMSO in the reaction phase and the inclusion of 2% BSA as blocking reagent in the capture phase.

Figure 3A:
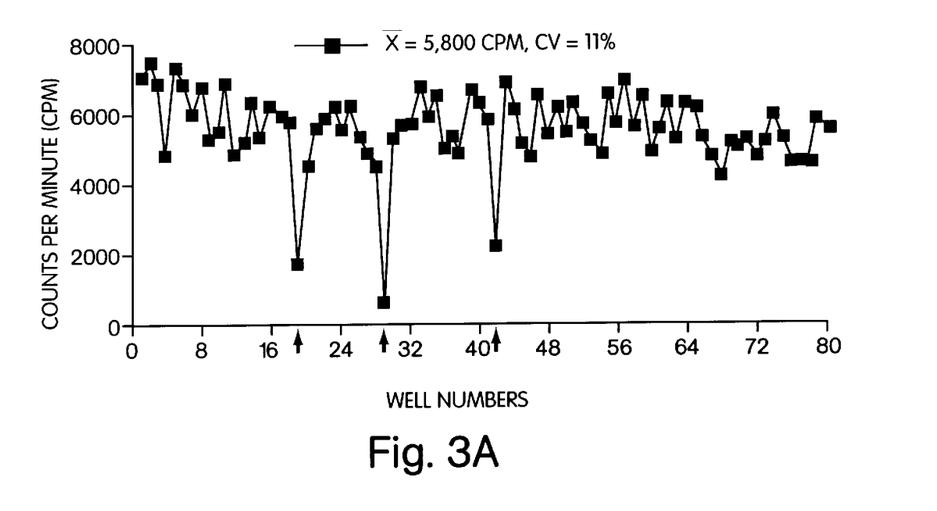
FIG. 3A is a graph showing the reproducibility of the transferase assay using the TCA precipitation method.
Figure 3B:
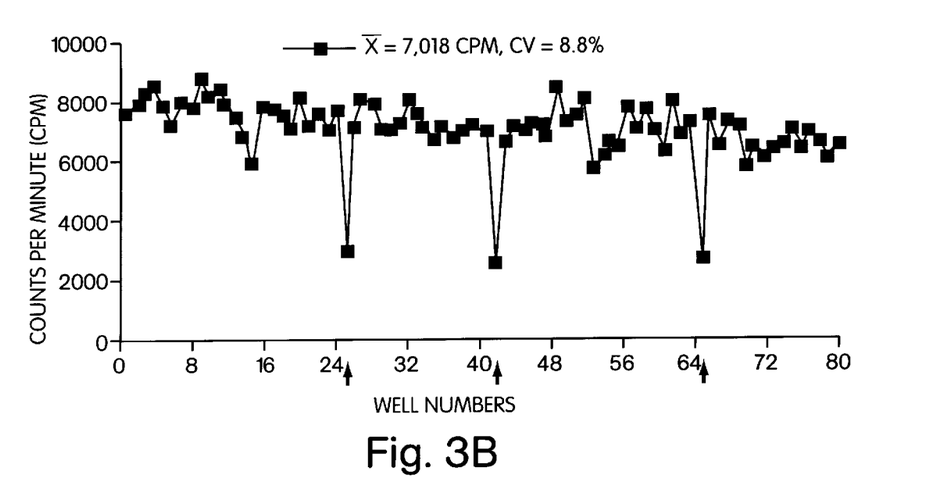
FIG. 3B is a graph showing the reproducibility of the transferase assay using the FlashPlate method.

Assay reproducibility and the ability to detect active compounds are critical performance criteria for a high throughput screen. A series of assay runs were made to determine the reproducibility of the assay and its ability to identify known inhibitors by TCA precipitation (FIG. 3A) and FlashPlate™ (FIG. 3B) methodologies. Transferase activity was measured by screening plates with wells containing DMSO (uninhibited or "negative" controls) and wells spiked with a standard inhibitor ($IC_{50}$ concentration) in DMSO (indicated by arrows). FIG. 3 shows the data generated by screening one plate by TCA precipitation methodology (FIG. 3A) and one plate by FlashPlate™ methodology (FIG. 3B). The mean cpm value (x) and intra-plate coefficient of variance (CV) of the uninhibited wells are shown. Wells containing inhibitor were readily identified by both TCA precipitation and FlashPlate™ methodologies.

The inhibition by a panel of compounds of transferase activity was measured by the TCA precipitation and Flash-Plate methodologies. Serial dilutions of test compounds in DMSO were assayed for inhibition of transferase activity according to the procedure described above in Methods. Table 2 shows the percent inhibition values obtained when compounds were tested at the same concentration by TCA precipitation and FlashPlate™ methodologies. The results show that percent inhibition values generated by both methodologies were comparable.

TABLE 2

Percent inhibition measurements of test compounds

| | Percent Inhibition | |
|---|---|---|
| | TCA | FlashPlate |
| Compound 1 | 94.0 | 94.2 |
| | 94.3 | 90.6 |
| Compound 2 | 45.5 | 40.8 |
| | 46.5 | 37.4 |
| Compound 3 | 97.2 | 94.1 |
| | 96.1 | 94.2 |
| Compound 4 | 33.9 | 39.2 |
| | 35.0 | 32.0 |
| Compound 5 | 99.6 | 99.9 |
| | 99.8 | 101.5 |
| Compound 6 | 54.4 | 47.4 |
| | 58.0 | 47.3 |
| Compound 7 | 82.6 | 80.8 |
| | 84.5 | 82.9 |

Figure 4:
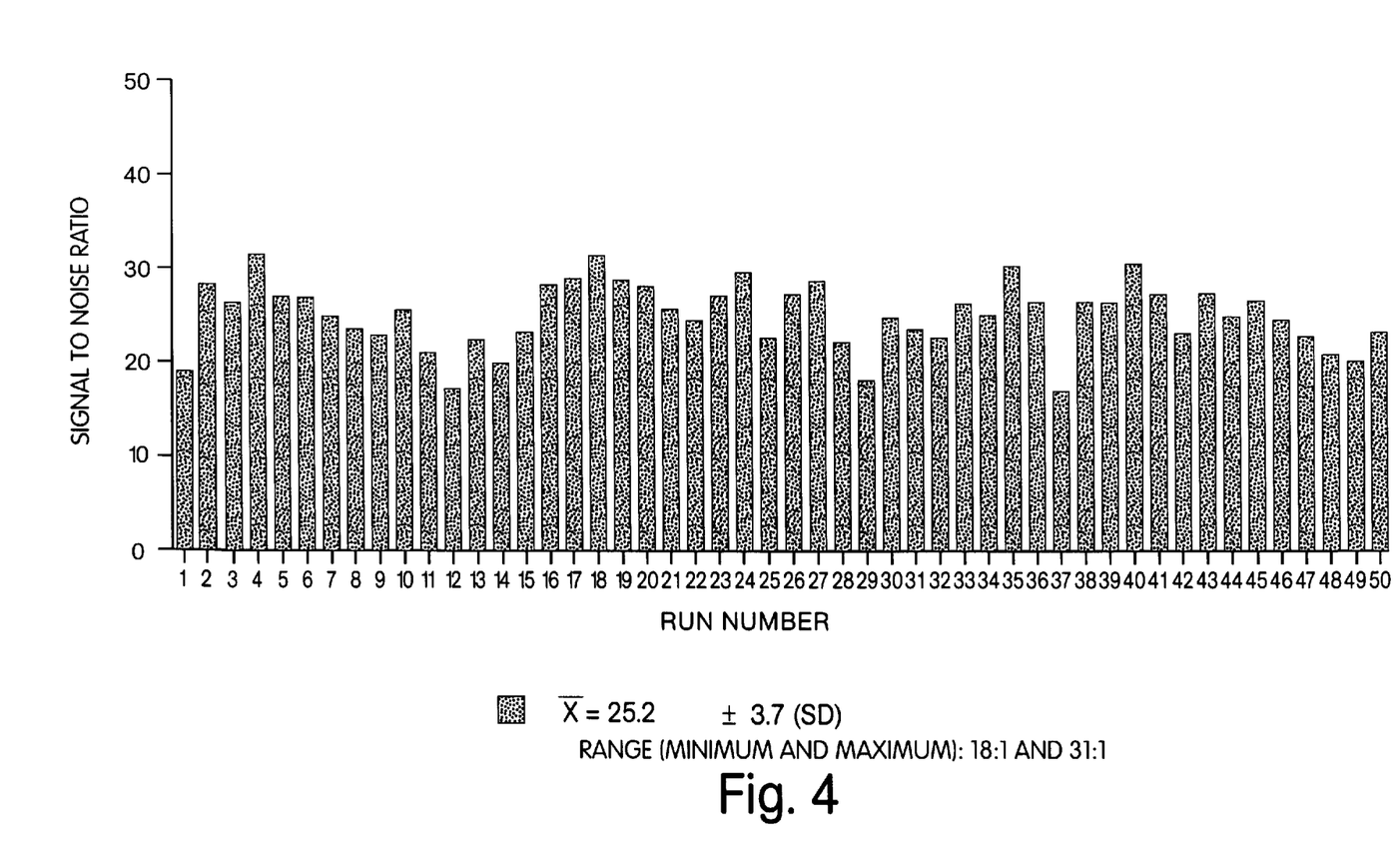
FIG. 4 is a chart showing the signal to noise ratio using FlashPlate methodology.

Data from multiple measurements of the transferase assay by TCA precipitation methodology and FlashPlate™ methodology were analyzed for reproducibility (n=38 plates). Data from 80 wells on each plate (excluding control wells) was analyzed. Each run contained at least 5 plates. Signal to noise ratio was calculated from uninhibited reactions (negative controls) and quenched reactions (blank controls) in each plate. The mean signal to noise ratio (x) and SD between individual runs are shown in FIG. 4. The intra-plate coefficients of variance (CV) ranged from 4.7%–18.3% with a mean CV of 11.5%+/−6.8% (SD) for the TCA precipitation methodology. In comparison, intra-plate CVs obtained using FlashPlate™ methodology ranged from 4.1%–10.9% with a mean CV of 7.5%+/−3.4% (SD). In 50 individual runs of the transferase assay utilizing FlashPlate™ methodology, a mean signal to noise ratio of 25.2+/−3.7 (SD) was observed, as shown in FIG. 4. The higher reproducibility of the FlashPlate™ methodology in comparison to the TCA precipitation methodology is probably due to the elimination of wash steps and fewer liquid handline, steps. These data show that the present metal-chelate capture methodology provides for a reliable HTS and stable signal to noise ratio.

Conclusion

A high throughput screen utilizing metal chelate capture technology has been developed. The assay evidences an high tolerance for several common assay reagents, including detergents, solvents and reducing agent. Measurement of enzymatic activity and of compound potency by Flash-Plate™ methodology is comparable to data generated by conventional TCA precipitation methodology.

Equivalents

Those skilled in the art will be able to ascertain many equivalents to the specific embodiments described herein. Such equivalents are intended to be encompassed by the following claims.

What is claimed is:

1. An assay method for determining the effect of a substance on the activity of an enzyme, comprising the steps of:
   a. combining a test compound with an enzyme capable of catalyzing the transfer of a detectable moiety to a substrate, a donor substance labeled with the detectable label, and a substrate specific for the enzyme comprising a metal-chelating moiety, and incubating the mixture under conditions sufficient to promote the enzymatic reaction;
   b. contacting the combination formed in (a) with a metal-derivatized solid phase under conditions sufficient to promote reaction of the immobilized metal and the chelating moiety; and
   c. detecting the signal generated.

2. The method of claim 1 wherein the enzyme comprises a prenyl transferase.

3. The method of claim 2 wherein the enzyme comprises farnesyl transferase or geranylgeranyl transferase.

4. The method of claim 2 wherein donor substance comprises a substance comprising a prenyl group capable of being transferred to a substrate by the action of the prenyl transferase.

5. The method of claim 2 wherein the substrate comprises a peptide or protein capable of being modified by the action of the prenyl transferase.

6. The method of claim 1 wherein the metal chelating moiety is a metal chelating peptide.

7. The method of claim 6 wherein the peptide comprises six histidine residues.

8. The method of claim 1 wherein the metal is selected from the group consisting of nickel, calcium, palladium, platinum, ruthenium and rhodium.

9. The method of claim 1 wherein the detectable label comprises a radioactive label.

10. The method of claim 9 wherein the radioactive label is selected from the group consisting of $^{3}H$, $^{14}C$, $^{35}S$, $^{125}I$, $^{45}Ca$, $^{33}P$ and $^{32}P$.

11. The method of claim 1 wherein the metal derivatized substrate comprises a solid phase having a scintillant disposed thereon and a metal immobilized thereon.

12. An assay method for determining the effect of a substance on the activity of a prenyl transferase enzyme, comprising the steps of:
   a. combining a test compound with a prenyl transferase enzyme, a radioactively-labeled donor substance, and a substrate specific for the prenyl transferase enzyme comprising a metal-chelating moiety, and incubating the mixture under conditions sufficient to promote the enzymatic reaction;
   b. contacting the combination formed in (a) with a metal-derivatized solid phase under conditions sufficient to promote reaction of the immobilized metal and the chelating moiety; and
   c. detecting the signal generated.

13. The method of claim 12 wherein the enzyme comprises farnesyl transferase or geranylgeranyl transferase.

14. The method of claim 12 wherein donor substance comprises a substance comprising a prenyl group capable of being transferred to a substrate by the action of the prenyl transferase.

15. The method of claim 12 wherein the substrate comprises a peptide or protein capable of being modified by the action of the prenyl transferase.

16. The method of claim 12 wherein the metal chelating moiety comprises six histidine residues.

17. The method of claim 12 wherein the metal is nickel.

18. The method of claim 12 the radioactive label is selected from the group consisting of $^{3}H$, $^{14}C$, $^{35}S$, $125I$, $^{45}Ca$, $^{33}P$ and $^{32}P$.

19. The method of claim 12 wherein the metal derivatized substrate comprises a solid phase having a scintillant disposed thereon and a metal immobilized thereon.

* * * * *